US008614343B2

(12) United States Patent
Smida

(10) Patent No.: US 8,614,343 B2
(45) Date of Patent: Dec. 24, 2013

(54) PROCESS FOR THE PRODUCTION OF A FATTY ACID/CARNITINE DERIVATIVE

(75) Inventor: Donya Smida, La Marsa (TN)

(73) Assignee: Lonza Ltd., Visp (CH)

( * ) Notice: Subject to any disclaimer, the term of this patent is extended or adjusted under 35 U.S.C. 154(b) by 335 days.

(21) Appl. No.: 13/148,072

(22) PCT Filed: Feb. 3, 2010

(86) PCT No.: PCT/EP2010/000654
§ 371 (c)(1),
(2), (4) Date: Aug. 5, 2011

(87) PCT Pub. No.: WO2010/089094
PCT Pub. Date: Aug. 12, 2010

(65) Prior Publication Data

US 2011/0295026 A1 Dec. 1, 2011

Related U.S. Application Data

(60) Provisional application No. 61/150,095, filed on Feb. 5, 2009.

(30) Foreign Application Priority Data

Feb. 5, 2009 (EP) .................................... 09001609

(51) Int. Cl.
*C07C 227/16* (2006.01)

(52) U.S. Cl.
USPC ........... 554/110; 554/108; 554/124; 554/130; 554/52; 514/556

(58) Field of Classification Search
None
See application file for complete search history.

(56) References Cited

U.S. PATENT DOCUMENTS 4,439,438 A * 3/1984 Cavazza ........................ 514/357
5,741,816 A 4/1998 Tsujihara et al.
7,842,726 B2 * 11/2010 Aoki et al. .................... 514/547

FOREIGN PATENT DOCUMENTS

WO 2005/115326 A1 12/2005

* cited by examiner

*Primary Examiner* — Yate K Cutliff
(74) *Attorney, Agent, or Firm* — Hoffmann & Baron, LLP

(57) ABSTRACT

The present invention discloses a process for the production of a fatty acid/L-carnitine derivative, whereby the educts are reacted in the presence of monochloroacetic acid.

7 Claims, No Drawings

PROCESS FOR THE PRODUCTION OF A FATTY ACID/CARNITINE DERIVATIVE

This application is the U.S. National Phase of, and Applicants claim priority from, International Patent Application Number PCT/EP2010/000654 filed Feb. 3, 2010, U.S. Provisional Patent Application bearing Ser. No. 61/150,095 filed Feb. 5, 2009, and European Patent Application bearing Serial Number 09001609.8 filed Feb. 5, 2009, which are incorporated herein by reference in their entirety.

BACKGROUND OF THE INVENTION

The present invention discloses a process for the production of a fatty acid/L-carnitine derivative using monochloroacetic acid.

3-Hydroxy-4-trimethylammonio-butanoate (henceforth "L-carnitine") is a quaternary ammonium compound biosynthesized from the amino acids lysine and methionine. In living cells, it is required for the transport of fatty acids from the cytosol into the mitochondria during the breakdown of lipids (or fats) for the generation of metabolic energy.

Fatty acid/L-carnitine derivatives like palmitoyl-L-carnitine are synthesised according to the state of the art by reacting the educts L-carnitine and the chloride of the fatty acid in the presence of gaseous HCl and a tri-halide acetic acid.

The U.S. Pat. No. 5,741,816 discloses a reaction of n-pentadecanoic acid with thionyl chloride and a subsequent reaction with L-carnitine in trichloroacetic acid.

However, there is still a need to improve upon these processes of the state of the art. In this regard, it would be advantageous to substitute the tri-halide acetic acid with an acid that has a lower molecular weight and a lower prize (currently at 4,338 USD per tonne for trichloroacetic acid).

DESCRIPTION OF THE INVENTION

The problems stated above are solved by the process according to the invention, which uses monochloroacetic acid in the production of a fatty acid/L-carnitine derivative. Said reagent has the advantage of a lower molecular weight and a prize which is smaller by a factor of 5.4 (currently at 800 USD per tonne).

"Derivative" according to the invention is the reaction product of L-carnitine and a fatty acid or fatty acid chloride, namely an esterified L-carnitine, whereby the hydroxyl moiety at carbon atom 3 of the L-carnitine has reacted with the acid or acyl chloride moiety of the fatty acid or fatty acid chloride to form the ester moiety.

Preferably, the monochloroacetic acid is used in a concentration of between 3.3 and 4.4 mol/L, even more preferably in a concentration of between 3.5 and 4.3 mol/L.

The chloride of the fatty acid is preferably used in a concentration of between 1.25 and 1.85 mol/L, even more preferably in a concentration of between 1.6 and 1.85 mol/L, while L-carnitine hydrochloride is preferably used in a concentration of between 1.2 and 1.5 mol/L, even more preferably in a concentration of between 1.2 and 1.4 mol/L The gaseous HCl is preferably used in a concentration of between 3 and 4 mol/L, even more preferably in a concentration of between 3.25 and 3.75 mol/L.

The reaction according to the invention preferably takes place at a temperature of between 70° C. and 80° C.

EXAMPLES

The invention will now be described in more detail by way of the following examples.

Comparative Example

Palmitoyl-L-carnitine hydrochloride in trichloroacetic acid 120 g L-carnitine and 368 g trichloroacetic acid are filled in the equipment and heated up to 73° C. After complete melting the solution is cooled down to 30° C. 27.5 g HCl gas are added to the reactor and the reaction is stirred for 1 h.

320.4 g palmitoyl chloride are slowly dosed over 1 hour and the solution is heated up to 50° C. and stirred for 1.5 hours.

195.3 g isopropanol and 498 g ethyl acetate are added at room temperature to the reaction mass, then cooled down to 0° C. The solid is filtrated and washed with 65.1 g isopropanol and 191.8 g ethyl acetate (precooled at 0° C.) and dried overnight.

The solid is recrystallized in 1050 ml isopropanol. The mixture is heated to 70° C. Isopropanol and ethyl acetate are added to the system and cooled to 0° C. 202.9 g palmitoyl-L-carnitine hydrochloride is obtained (74% yield). Its melting point is determined at 164-184° C.

H-NMR (500 MHz, DMSO) δ 0.85 (t, 3 H); 1.25 (m, 24 H), 1.55 (m, 2 H), 2.35 (m, 2 H), 2.7 (d, 2 H), 3.12 (s, 9 H), 3.65 (d, 1 H), 3.85 (dd, 1 H), 5.45 (m, 1H)

Example 1

Palmitoyl-L-carnitine hydrochloride in monochloroacetic acid 100 g L-carnitine and 180 g monochloroacetic acid are filled in the equipment and heated up to 70° C. After complete melting the solution is cooled down to 30° C. 24 g HCl gas are added to the reactor, the reaction is stirred for 1 h at 50° C.

213 g palmitoyl chloride are slowly dosed over 1 hour and the solution is heated up to 70° C. and stirred for 2 hours.

1000 g Acetone are added at room temperature. The solid is filtered out, washed with 500 g acetone and dried at 60° C. and 14 mbar overnight.

The solid is recrystallized with 450 g Acetone. 202.9 g palmitoyl-L-carnitine hydrochloride is obtained (74% yield). Its melting point is determined at 164-184° C.

H-NMR (500 MHz, DMSO) δ 0.85 (t, 3 H); 1.22 (m, 24 H), 1.5 (m, 2 H), 2.3 (m, 2 H), 2.7 (d, 2 H), 3.1 (s, 9 H), 3.65 (d, 1 H), 3.85 (dd, 1 H), 5.45 (m, 1H)

Example 2

Lauryl-L-carnitine hydrochloride 20.0 g L-Carnitine hydrochloride and 25.3 g monochloroacetic acid are filled in the equipment and heated up to 70° C. After complete melting the solution is cooled down to 50° C.

29.6 g lauryl chloride is slowly dosed over 1 hour and the solution is heated up to 70° C. and stirred for 3 hours.

After dosing 30.7 g isopropanol at room temperature and termination of the exothermic reaction, 135.2 g ethyl acetate is added and the suspension is cooled down to 3° C. overnight.

The solid is filtered out and washed with 147.8 g isopropanol/ethyl acetate (1:2.7) and dried at 50° C. and 24 mbar overnight.

34.2 g lauryl-L-Carnitine hydrochloride is obtained.

A yield of 99.4% is achieved. The melting point of the final product is determined at 177° C.

H-NMR (500 MHz, DMSO) δ 0.86 (t, 3 H), 1.24 (m, 16 H), 1.52 (m, 2 H), 2.31 (m, 2 H), 2.68 (d, 2 H), 3.1 (s, 9 H), 3.61 (d, 1 H), 3.8 (dd, 1 H), 5.45 (m, 1H)

Example 3

Octanoyl-L-carnitine hydrochloride 20.0 g L-Carnitine hydrochloride and 25.3 g monochloroacetic acid are filled in the equipment and heated up to 70° C. After complete melting the solution is cooled down to 50° C.

22.0 g octanoyl chloride is slowly dosed over 30 minutes and the solution is heated up to 70° C. and stirred for 3 hours.

After slowly dosing 30.8 g isopropanol at room temperature and termination of the exothermic reaction, 104.5 g ethyl acetate is added and the suspension is cooled down to 3° C. overnight.

The solid is filtered out and washed with 147.8 g isopropanol/ethyl acetate (1:2.7) and dried at 50° C. and 24 mbar overnight.

25.4 g octanoyl-L-carnitine hydrochloride is obtained.

A yield of 81.1% is achieved. The melting point of the final product is determined at 178-181° C.

H-NMR (500 MHz, DMSO) δ 0.85 (t, 3 H), 1.25 (m, 8 H), 1.5 (m, 2 H), 2.3 (m, 2 H), 2.7 (d, 2 H), 3.1 (s, 9 H), 3.65 (d, 1 H), 3.8 (dd, 1 H), 5.45 (m, 1 H)

The invention claimed is:

1. A process for the production of a fatty acid/L-carnitine hydrochloride derivative, whereby the educts are reacted in the presence of monochloroacetic acid.

2. The process according to claim 1, whereby the educts are the chloride of a fatty acid and L-carnitine.

3. The process according to claim 1, whereby the fatty acid is selected from the group consisting of palmitic acid, lauric acid and octanoic acid.

4. The process according to claim 1, whereby the monochloroacetic acid is used in a concentration of between 3.3 and 4.4 mol/L, preferably in a concentration of between 3.5 and 4.3 mol/L.

5. The process according to claim 1, whereby the chloride of the fatty acid is used in a concentration of between 1.25 and 1.85 mol/L, preferably in a concentration of between 1.6 and 1.85 mol/L.

6. The process according to claim 1, whereby L-carnitine is used in a concentration of between 1.2 and 1.5 mol/L, preferably in a concentration of between 1.2 and 1.4 mol/L.

7. The process according to claim 1, whereby the reaction takes place at a temperature of between 70 and 80° C.

* * * * *